United States Patent [19]

Ecanow

[11] Patent Number: 4,849,405
[45] Date of Patent: Jul. 18, 1989

[54] ORAL INSULIN AND A METHOD OF MAKING THE SAME

[75] Inventor: Bernard Ecanow, Wilmette, Ill.

[73] Assignee: Synthetic Blood Corporation, Deerfield, Ill.

[21] Appl. No.: 835,550

[22] Filed: Mar. 3, 1986

Related U.S. Application Data

[63] Continuation-in-part of Ser. No. 608,483, May 9, 1984, abandoned.

[51] Int. Cl.⁴ ............................................. A61K 37/26
[52] U.S. Cl. ...................................................... 514/3
[58] Field of Search ............................................ 514/3

[56] References Cited

U.S. PATENT DOCUMENTS

| | | | |
|---|---|---|---|
| 4,343,797 | 8/1982 | Ecanow | 514/2 |
| 4,356,167 | 10/1982 | Kelly | 424/38 |
| 4,394,372 | 7/1983 | Taylor | 424/85 |
| 4,439,424 | 3/1984 | Ecanow et al. | 424/153 |
| 4,448,765 | 5/1984 | Ash et al. | 424/14 |

Primary Examiner—Frederick E. Waddell
Attorney, Agent, or Firm—Mason, Kolehmainen, Rathburn & Wyss

[57] ABSTRACT

The present invention provides for a composition of matter useful as an oral dosage form of insulin based upon a two phase liquid aqueous system in which insulin component or components are incorporated. The invention also provides for a method of preparing the oral dosage form of insulin, as well as a further process whereby sustained release dosage forms of oral insulin are produced. The oral form of insulin eliminates or reduces the need to use injection as a mode of administering insulin.

3 Claims, No Drawings

ORAL INSULIN AND A METHOD OF MAKING THE SAME

This application is a continuation-in-part of U.S. Ser. No. 608,483 filed May 9, 1984.

This invention concerns an improved form of insulin which is orally administered, and methods of preparation.

Review of the scientific literature indicates that despite intensive research, the problems obstructing the development of an oral dosage form of insulin remain unsolved. The published research includes no report of a delivery system that will make it possible to administer insulin orally. (Reference: Chemical Abstracts 1970–1984)

The investigations of Dapergolas and Gregoriadis suggest that a moderately effective hypoglycemic effect may be achieved through the intragastric use of liposome entrapped insulin. Examination of the data of these experiments indicate that the rate of insulin absorption was erratic and further, that it was not possible to determine the quantity of insulin that was absorbed. (Reference: Dapergolas, G. and Gregoriadis, G. Hyperglycemic Effect of Liposome Entrapped Insulin Administered Intragastrically Into Rats; Lancet, Oct. 16, 1976, pp. 824–827)

The use of liposomes to prepare an oral form of insulin is based upon a concept and a method manufacture that differs fundamentally from the concept and method of the herein disclosed invention. A two phase coacervate system comprises the basis of this invention; it bears no relationship to liposomes. Moreover, given the known difficulties in the manufacture and use of liposomes, such compositions do not appear to be the basis on which a useful oral insulin may be developed. (Reference: Ostro, Marc, Lipsomes, Marcel Dekker, New York, 1983)

The advantages of an oral dosage form of insulin are readily apparent. An oral form of insulin will eliminate or reduce the need to use injection as the mode of administering insulin. Further, it appears that an oral form of insulin could be used to advantage in the treatment of adult onset diabetes mellitus. The sulfonylureas are now prescribed for the treatment of this form of diabetes despite the adverse effects associated with the use of this class of drugs. The sulfonylureas are not considered to be an acceptable substitute for insulin nor are they considered to be oral forms of insulin.

It is important to note that no known oral dosage form of insulin has been developed since the discovery of insulin more than sixty years ago.

The present invention discloses an oral dosage form of insulin and a method by which said insulin can be prepared. However, it should be noted that the herein disclosed invention constitutes a safe, effective oral dosage form not only for insulin but for non-polar drugs and other medical compositions known to be subject to degradation in the digestive system.

Examples of the applicants' discovery of coacervate systems by means of which drugs, enzymes, nutrients and hemoglobin may be introduced into and transported in the circulatory system are disclosed in U.S. Pat. Nos. 4,343,797 and 4,439,424. In the present disclosure, the concepts of the inventions referred to above have been modified and utilized in a manner that yields an oral as opposed to an intravenous preparation. Moreover, the specific use of the coacervate system of this invention distinguishes, the claimed composition and its method of preparation from the known microencapsulated biologicals and drug products and the methods used to produce them. At this point, the state of the art does not include an oral composition which will protect drugs, biologicals and other medical preparations vulnerable to degradation by enzymes, pH, acid-base balance and other conditions and processes of the gastrointestinal tract.

It is an object of this invention to provide a delivery system that enables the safe, effective oral administration of the known forms of insulin. When insulin is incorporated in the herein disclosed delivery system it retains all of its known pharmacologic and physiological properties. Furthermore, this invention provides a convenient method of preparation of the claimed oral dosage forms.

The invention provides a composition of matter useful as an oral dosage form of insulin; said preparation comprising a non-toxic two phase liquid system, both phases being aqueous;

(a) one of said phases being a relatively nonpolar coacervate phase;

(b) The other of said phases being a relatively polar liquid aqueous phase;

(c) said relatively non-polar coacervate phase being insoluble in and in equilibrium with said relatively polar liquid aqueous phase;

(d) said two phase system, when prepared to contain an insulin component or components in the coacervate phase of the coacervate system, yields a delivery system for the oral administration of insulin.

Moreover, the invention provides for a method of preparing a composition useful as an oral dosage form of insulin, said method based upon the two phase liquid system. A preferred method is characterized by the steps of (a) combining albumin and lecithin in equal proportions in sterile water; (b) thoroughly mixing the components; (c) storing said mixture undisturbed until the composition of step (a) separates into two layers, one above the other, the lower phase being a substantially non-polar coacervate phase, the upper phase being an equilibrium water phase; (d) continuing the separation process until no increase in the volume of the coacervate system can be observed; (e) centrifuging the composition until inspection reveals a clear demarcation of the two phases and (f) separating the two phases.

Given that no oral dosage form of insulin now exists, the herein disclosed invention represents a significant scientific and medical advance. By using any one of a number of appropriate non-toxic coacervate systems as a beginning step in the manufacture of this invention, it becomes possible, through a subsequent sequence of relatively simple processing steps to produce a delivery system for the oral administration of insulin. The said system can be produced as a liquid or as an encapsulated composition.

In this disclosure, the term particle refers to encapsulated or emulsion droplet entities. In the claimed invention, the size of the particles which will contain the hemoglobin component may range from nanometer size to micron size; from $10^{-8}$ microns to 10 microns. Particles in this range of sizes are known to pass through the wall of the small intestine and, it follows, into the circulatory system. There is reason to believe that in the finished product of this invention, the coacervated micro and sub-micro encapsulated particles will tend to adhere to the membrane of the gastrointestinal tract, thereby facilitating passage through the wall of the small intestine.

Another singularly important feature of this invention is the protection afforded the insulin component of this composition from enzymatic degradation in the digestive tract. This is accomplished by incorporating the insulin in the coacervate phase of the coacervate system. In the process of this incorporation, a film of coacervate phase water surrounds and coats each insulin molecule. This feature is of fundamental importance since coacervate phase water differs in physical chemical structure from the bulk water present in the stomach. The digestive enzymes which degrade insulin readily diffuse in the aforementioned bulk water, however, since these enzymes diffuse only minimally, if at all, in the water of the coacervate phase. The rate of interaction between the insulin component and the digestive enzyme is extremely slow. Since the rate of interaction is so slow, physiologically useful quantities of insulin escape destruction, pass through the wall of the small intestine and into the circulation. Moreover, in this invention, the insulin component is protected from the degradation effects of pH, acid-base balance and other conditions and processes of the gastrointestinal tract.

In the manufacture of the claimed composition, any of the known forms of insulin, i.e., regular insulin, globin zinc insulin, insulin zinc suspension, prompt insulin zinc suspension, extended insulin zinc suspension, or combinations thereof may be used. The insulins used in this invention may be of U.S.P. standard, if desired. Non U.S.P. insulins may be used provided they are acceptable in other fundamental respects.

If preferred, the insulin component may be comprised of recrystallized insulin obtained from animal, recombinant genetic, synthetic or other sources. Since the claimed compositions are intended only for oral use, the insulin used in this invention need not be subjected to the rigorous manufacturing steps required for U.S.P. injectable insulin. However, if desired, insulin prepared for injection may be used in this invention.

The claimed composition may be prepared to any of several specifications. Thus, it may consist of insulin dispersed in the disclosed coacervate system and dispensed as a liquid preparation. The method of this invention also provides for additional steps in which the previously described preparation is further processed to yield a product which is comprised of particles of encapsulated insulin. The particles are within the size range referred to previously. The final product can be placed in conventional gelatin capsules and dispensed as such, or alternatively, the particles containing insulin can be dispensed in any suitable liquid vehicle, i.e., a vehicle based on coacervate phase water and dispensed for use in that form. The invention provides for sustained release dosage forms and for emulsion and suspension preparations.

Any appropriate non-toxic coacervate system can be used in the manufacture of the product of this invention. Further, any endogenous biological surface active agent or derivatives thereof, e.g., albumin, lecithin, gelatin, etc., can be used to make a coacervate system appropriate for the product and process of this invention. Alternatively, suitable non-toxic exogenous components can also be used to prepare the coacervate system, for example, acacia when combined with gelatin. Many other surface active agents and/or combinations thereof that can form multiple coacervate phase systems can also be used. However, it is fundamental to the claims of this invention that regardless of the constituent ingredients used, the first manufacturing step involves this preparation of an appropriate coacervate system. Upon completion of this step, the coacervate system will consist of two phases: (1) an internal suspension, relatively non-polar phase, commonly referred to as the coacervate phase, and (2) an associated, relatively polar, external suspension or equilibrium phase. These phases are insoluble in and in equilibrium with each other. The coacervate phase of the disclosed coacervate system can comprise from 0.5 to 99.5% by volume of the system; correspondingly, the associated equilibrium phase can comprise from 0.5 to 99.5% by volume of the herein described coacervate system.

In order to explain the claimed composition and method of this invention, the following is a description of the preferred method of manufacture of said composition and the composition itself. Specific examples which follow will explain and illustrate the variety of formulations that are possible within the parameters of this disclosure.

As noted previously, preparation of an appropriate coacervate system comprises the first step in the manufacture of the claimed composition of matter. The said coacervate system may be formulated using any acceptable non-toxic biological, non-biological surface active agent, derivatives or mixtures thereof. Sources of the surface active agent component may be either of natural or synthetic origin. Any of the following are examples of acceptable surface active agents: albumin, suitable phospholipids, gelatin, modified fluid gelatin, acacia gel and other surface active compositions known to those skilled in the art. In this invention, appropriate combinations of these agents are preferred.

In the method of this invention, the combination of albumin and a phospholipid, preferably lecithin is preferred. Other phospholipids such as cephalin, isolecithin, sphingomyelin, phosphatidyl serine, phosphatidic acid, phosphatidyl inositol and phosphatidyl choline may be used in place of the preferred lecithin.

In the preferred method of this invention, equal weight to volume proportions of albumin and lecithin are added to a quantity of sterile water that will yield 100 mls of aqueous solution. Any quantity of albumin and lecithin can be used, provided that the proportions given above are observed and the quantity of water is adjusted accordingly. Three per cent weight to volume of lecithin and three per cent weight to volume of albumin is preferred. Unequal proportions of these compositions may be used to produce a coacervate system; however, while such systems may have useful characteristics, unequal proportions are not believed to be preferable i.e.; drug transport, etc., for this invention.

In the method of this invention, other combinations of surface active agents may be used. These combinations would include the following: acacia gel and gelatin or modified gelatin, two gelatins of the same or differing isoelectric points, two modified fluid gelatins of the same or differing isoelectric points and other combinations of surface active agents known to those skilled in the art.

Following the step in which albumin and lecithin are added to sterile water, the solution is thoroughly mixed and stored, undisturbed in suitable containers. The storage step takes place at a temperature which can range from the freezing point to 4° C. to room temperature. In the disclosed preferred method storage takes place at any temperature within the range of 4° to 15° C.

During the period of storage, the solution described above will separate into two phases. The upper phase (layer) is referred to as the equilibrium water phase. The lower phase (layer) is referred to as the coacervate phase. The period of storage is continued until the maximum yield of the coacervate phase of the coacervate system has been achieved. Maximum yield is the point in the manufacturing process at which no significant increase in the volume of the coacervate phase can be observed. This determination may be made by visual inspection or other suitable means. As is known to those skilled in the art, longer periods of storage will produce greater yields of the coacervate phase.

When it is determined that the maximum yield of the coacervate phase has been achieved, the coacervate system is centrifuged until observation indicates that a clear division exists at the interface of the two phases of the coacervate system. At this point, the two phases are separated from each other by means of a separatory funnel. The desired amount and type of insulin is then added to the coacervate phase and mixed thoroughly.

Any of the known forms and dosages of insulin, i.e., regular insulin, globin zinc insulin, insulin zinc suspension, prompt insulin zinc suspension, extended insulin zinc suspension, protamine zinc insulin or combination thereof may be used. The insulin(s) used may be of U.S.P. standard. If preferred, the insulin component may be one directly derived from recrystallization of insulin from animal, recombinant genetic or other sources. The invention contemplates the manufacture of a variety of oral insulin preparations, compositions and dosages in order to meet specific medical requirements. Accordingly, no single insulin specification can be described as preferred. For purposes of this disclosure, the individual dose can be 100 standard units and/or fractions and/or multiples thereof.

After the step in which the insulin component is dispersed in the coacervate phase and thoroughly mixed, the preparation may be dispensed as an oral dosage form of insulin. Preferably, the manufacturing process is continued. In that case, the next procedure involves the recombination of the equilibrium water phase and the coacervate phase which now contains the insulin component.

Following the recombination of the phases, the preparation is emulsified using a colloid mill, sonifier or other emulsifying technique known to those skilled in the art. The particles of the emulsion may range in size from $10^{-8}$ microns to 10 microns. It is preferred that the particle size be within the nanometer and millimicron range.

The product resulting from the emulsifying step comprises a prompt release form of insulin and may be used as such or stored under refrigeration until needed. The emulsified composition is, if desired, processed further to produce time release, i.e., sustained release forms of insulin(s). To produce these forms of insulin, the preparation is subjected to a heating step, i.e., the preparation is heated for from 30 seconds to 15 minutes at a temperature which may range from 20° to 70° C. Since this step will harden the surface film surrounding each particle, the variables of time and temperature may be varied to produce a spectrum of particle surface film hardnesses. This method comprises the preferred method. Other processes may be used to prepare sustained release forms of the claimed composition. Thus, a cross linking agent, such as a non-toxic entity within the aldehyde group, i.e., gluteraldehyde may be used in a chemical process which harden the film surface of the particles containing the insulin component.

As a result of the heating step, the claimed oral insulin composition is comprised of particles which are characterized by differing degrees of surface film hardness and thus, differing rates of time release. After the heating step is completed, the composition is filtered through a filter pad. The product remaining in the filter bed constitutes the particles of oral insulin. These are removed from the filter bed by a washing step and then dried by any acceptable drying process. Upon completion of the drying step, the preparation of particles containing oral insulin is completed. The composition may now be placed in an appropriate oral dosage form. Thus the desired dose of the composition may be resuspended in a suitable non-toxic liquid vehicle, or placed in other conventional oral dosage forms and dispensed or stored, preferably under refrigeration until needed. If it is desired, an appropriate dose of the prompt release particles may be mixed with an appropriate dose of the previously described time release oral insulin(s) formulation. This mixture is then placed in any acceptable, non-toxic oral dosage form and dispensed or stored, preferably under refrigeration until needed.

Previously, in this disclosure it was stated that a number of entities may be used to prepare the required coacervate system. An example of an alternative acceptable coacervate system for preparing oral insulin is based on the use of gelatin. In this alternative, the following steps are used to produce the coacervate system. Five per cent gelatin solution is dispersed in distilled water and heated to 40° C. 0.9% sodium chloride solution is slowly added to the preparation until the solution separates into two layers. The lower layer comprises the colloid rich liquid gelatin or coacervate phase. The upper layer consists of the equilibrium water phase.

The two phases are separated by means of a separatory funnel. The desired quantity and type of insulin or combinations thereof, as described above, are then added and mixed into the coacervate phase, and may, if desired, be dispensed as oral liquid insulin. If preferred, the manufacturing process proceeds and the two previously separated phases, one of which now contains insulin, are recombined. Through the use of any acceptable emulsifying technique, an emulsion consisting of nanometer, millimicron and micron size particles inside of which insulin is contained is prepared. The emulsion is simultaneously rapidly cooled and stirred at a temperature of from 0° to 10° C. for from 15 to 60 minutes by means of a refrigerated stirring unit. After this stirring step, the composition is forced through a filtering system. The product remaining in the filter bed is removed through a washing step. Upon completion of this step the particles are dried in an air drying system. When the encapsulated particles of insulin are completely dried, the quantity and type of insulin necessary for a specific dose is placed in any appropriate oral drug delivery system. The conventional gelatin capsule is preferred.

SPECIFIC EXAMPLES

Examples of how the claimed composition(s) of matter may be prepared follow:

EXAMPLE 1

5% weight to volume proportions of albumin and lecithin are added to an amount of distilled water that will yield 100 mls of aqueous solution. The mixture is then thoroughly mixed by a vortex mixer. Following the mixing step, the solution is stored undisturbed until the maximum yield of the coacervate phase of the coacervate system has been achieved. The storage step takes place at 4° C. When it is observed that the maximum yield of the coacervate phase has been achieved, the coacervate system is centrifuged until observation indicates that a clear division exists at the interface of the two phases of the coacervate system. The two phases are then separated by means of a separatory funnel. The equilibrium water phase resulting from this separation step is set aside for subsequent recombination with the coacervate phase. Next, 100 standard units of regular insulin U.S.P. is thoroughly mixed into the coacervate phase. Following this step, the two phases are recombined and subjected to an emulsifying procedure to produce an emulsion, the particles of which will range from the nanometer to the millimicron size. The emulsified product comprises a prompt release form of insulin and may be used as such or stored, preferably under refrigeration, until needed.

EXAMPLE 2

The method of Example 1 is followed except that Extended Insulin Zinc Suspension U.S.P. is used in place of regular insulin and the particles removed from the filtration bed are placed in gelatin capsules in doses that are medically appropriate.

EXAMPLE 3

The method of Example 1 is followed except that Prompt Insulin Zinc Suspension U.S.P. is used in place of regular insulin.

EXAMPLE 4

The method of Example 1 is used except that Globin Zinc Insulin Suspension U.S.P. is used in place of regular insulin. A mixture of the produce of the emulsification step and the product subjected to the heating step is prepared and dispensed in an appropriate liquid dosage form.

EXAMPLE 5

The method of Example 1 is used except that Protamine Zinc Insulin is used in place of regular insulin.

EXAMPLE 6

The method of Example 1 is used except that a mixture of regular insulin U.S.P. and Insulin Zinc Suspension U.S.P. are used in place of regular insulin.

EXAMPLE 7

200 mls of 5% solution of albumin is added to 200 mls of 3% solution of lecithin and mixed thoroughly. The remaining steps of the procedure follow those of Example 1, except that Protamine Zinc Insulin are used in place of regular insulin.

EXAMPLE 8

200 mls of a 5% solution of albumin is added to 200 mls of a 7% solution of lecithin and mixed thoroughly. The remaining steps of the procedure follow Example 1, except that Globulin Zinc Insulin Suspension U.S.P. is used in place of Regular Zinc Insulin.

EXAMPLE 9

200 mls of a 3% solution of albumin is thoroughly mixed with 200 mls of a 3% solution of isolecithin. The solution is then stored undisturbed at 4° C. for 24 hours. The remaining steps of the procedure follow Example 1.

EXAMPLE 10

Disperse 6% gelatin solution in distilled water and heat to 40° C. Next, slowly add that amount of sodium chloride to the solution as will result in a two phase system. The lower layer comprises the colloid rich liquid gelatin phase, the upper layer constitutes the coacervate phase. The two phases are separated and 100 units of regular insulin U.S.P. is added to the coacervate phase. Recombine the two phases, mix thoroughly and through the use of a colloid mill prepare an emulsion of the recombined phases wherein the size of the particles of said emulsion are in the range of $10^{-8}$ microns. Following the emulsifying step, the emulsion is simultaneously rapidly cooled and stirred at a temperature of 5° C. for 30 minutes. The resulting particles are thoroughly rinsed with distilled water following which they are completely dried. The quantity of the composition placed in gelatin capsules is a function of the medically indicated dosage of insulin or combinations thereof. The particles are then placed in gelatin capsules in the dosages and types of insulin desired.

EXAMPLE 11

The method of Example 9 is followed except that Isophane Insulin Suspension U.S.P. is used in place of regular insulin U.S.P.

EXAMPLE 12

The method of Example 1 is followed except that Extended Insulin Zinc Suspension U.S.P. is used in place of Regular Insulin U.S.P.

EXAMPLE 13

The method of Example 1 is followed except that Lente Insulin is used in place of regular insulin.

EXAMPLE 14

The method of Example 1 is followed except that recrystallized insulin directly derived from animal sources is used in place of Regular Insulin U.S.P.

EXAMPLE 15

The method of Example 1 is used except that a combination of regular and globin zinc insulin are used in place of regular insulin.

EXAMPLE 16

200 mls of a 3% solution of albumin is thoroughly mixed with 200 mls of a 3% solution of isolecithin. The solution is then stored undisturbed at 4° C. for 24 hours. The remaining steps of the procedure follow Example 1, except that Prompt Insulin Zinc Suspension U.S.P. is used in place of regular insulin U.S.P.

EXAMPLE 17

The method of Example 1 is used except that a combination of Regular Insulin U.S.P., Prompt Zinc Suspension and Extended Insulin Zinc Suspension is used in place of regular insulin.

EXAMPLE 18

The method of Example 1 is used except that after the two phases of the coacervate system are separated, 10 units of regular insulin are dispersed into the coacervate phase and mixed thoroughly. The composition is then dispensed as oral liquid insulin or placed in refrigerated storage until it is to be dispensed.

EXAMPLE 19

The method of Example 10 is followed except that after two phases of the system are separated 20 units of insulin are dispersed in the coacervate phase and mixed thoroughly. The preparation can either be dispensed as an oral liquid insulin preparation or stored until needed.

EXAMPLE 20

Example 1 is followed except that the final product of said example is heated for 20 seconds at a temperature of 40° C. Following the heating step, the composition is forced through a filter bed. The product remaining in the filter bed is removed through a washing procedure and then dried. Upon completing of the drying step, the composition may be placed in any acceptable oral dosage vehicle in the indicated dose.

EXAMPLE 21

Example 1 is followed except that the heating step is carried out for 10 seconds at 35° C.

EXAMPLE 22

Example 1 is followed except that 0.5% weight to volume of gluteraldehyde is added to the final product of said example. The composition is mixed thoroughly and then subjected to a filtering step. The particulate matter remaining in the filter bed is removed and placed in refrigerated storage for three to five hours, after which the composition is washed with distilled water until no trace of the gluteraldehyde is found in the wash water. This step is followed by a period of drying, after which the product of the drying step may be placed in any suitable dose in any conventional oral dosage vehicle.

EXPERIMENT

Two white laboratory rats, weighing 177 and 197 grams, respectively, were used in this experiment. One rat was administered a preparation of oral insulin according to the present invention containing 5 units of insulin; a formulation of the oral insulin according to the present invention containing 10 units of bovine insulin was administered to the second rat. Blood samples were drawn from each animal before and three hours after administration of the oral insulin preparation. The results given below are expressed as the percentage of the pre-experiment blood glucose level.

| Animal | Units of Bovine Insulin | Result |
| --- | --- | --- |
| 1 | 5 | 66.3% of initial blood glucose level |
| 2 | 10 | 47.1% of initial blood glucose level |

One white laboratory rat weighing 181 grams received a non-encapsulated preparation containing 5 units of free bovine insulin. This animal served as the control. After three hours, blood glucose level was 98.7% of the pre-experiment blood glucose level.

I claim:

1. A method of introducing insulin into a circulatory system comprising orally ingesting a composition comprising an aqueous coacervate system including water, a surface active agent and an effective amount of insulin, said coacervate system including an aqueous coacervate-based film encapsulating the insulin; said aqueous coacervate-based film comprising an aqueous colloid-rich phase, or an aqueous equilibrium water phase, or a combination thereof.

2. A method of adding insulin to the circulatory system of a mammal comprising having the mammal orally ingest a composition comprising an aqueous coacervate phase derived from a two-phase coacervate system, said coacervate phase including water, a surface active agent and an effective amount of insulin, said aqueous coacervate phase including an aqueous coacervate-based film encapsulating the insulin.

3. A method of treating diabetes comprising having a diabetic orally ingest an effective amount of a composition comprising an aqueous coacervate phase derived from a two-phase coacervate system, said coacervate phase including water, a surface active agent and an effective amount of insulin, said aqueous coacervate phase including an aqueous coacervate-based film encapsulating the insulin.

* * * * *